United States Patent
Balla et al.

(10) Patent No.: US 8,101,769 B2
(45) Date of Patent: Jan. 24, 2012

(54) PROCESS FOR PREPARING ETHYL (S)-2-ETHOXY-4-[N-[1-(2-PIPERIDINOPHENYL)-3-METHYL-1-BUTYL] AMINOCARBONYL METHYL]BENZOATE AND USE THEREOF FOR THE PREPARATION OF REPAGLINIDE

(75) Inventors: Venkata Sasidhar Balla, Bangalore (IN); Madhubabu Alapharthi, Bangalore (IN); Nitin Sharadchandra Pradhan, Maharashtra (IN); Jon Valgeirsson, Hafnarfjorour (IN)

(73) Assignee: Actavis Group PTC EHF (IE)

( * ) Notice: Subject to any disclaimer, the term of this patent is extended or adjusted under 35 U.S.C. 154(b) by 1015 days.

(21) Appl. No.: 12/031,184

(22) Filed: Feb. 14, 2008

(65) Prior Publication Data
US 2008/0200684 A1 Aug. 21, 2008

(30) Foreign Application Priority Data
Feb. 15, 2007 (IN) .............................. 311/CHE/2007

(51) Int. Cl.
*C07D 211/22* (2006.01)
(52) U.S. Cl. ........................................................ 546/234
(58) Field of Classification Search .................. 546/234
See application file for complete search history.

(56) References Cited

U.S. PATENT DOCUMENTS

| 5,312,924 | A | 5/1994 | Grell et al. |
|---|---|---|---|
| 7,148,355 | B2 * | 12/2006 | Ray et al. .................. 546/234 |
| 2007/0123564 | A1 | 5/2007 | Heck et al. |

FOREIGN PATENT DOCUMENTS

| WO | 9300337 | | 1/1993 |
|---|---|---|---|
| WO | 03027072 | A1 | 4/2003 |
| WO | 2004103983 | A1 | 12/2004 |

OTHER PUBLICATIONS

Ray et al. "Industrial process . . . . . . " CA138:287529 (2003).*
Tang et al. "Boric acid . . . . . " Organic syn. v.81p. 262-267 (2005).*
International Search Report and Written Opinion; International Application No. PCT/IS2008/000825; International Filing Date Feb. 15, 2008; Date of Mailing Aug. 4, 2008; 13 pages.

* cited by examiner

*Primary Examiner* — Celia Chang
(74) *Attorney, Agent, or Firm* — Cantor Colburn LLP

(57) ABSTRACT

Described herein is an improved, commercially viable and industrially advantageous process for the preparation of Repaglinide intermediate, ethyl (S)-2-ethoxy-4-[N-(1-(2-piperidino-phenyl)-3-methyl-1-butyl)-aminocarbonylmethyl]-benzoate. The process provides the Repaglinide intermediate in higher yield and purity compared to the previously disclosed processes, thereby providing for production of Repaglinide and its pharmaceutically acceptable salts in high purity and in high yield.

12 Claims, No Drawings

PROCESS FOR PREPARING ETHYL (S)-2-ETHOXY-4-[N-[1-(2-PIPERIDINOPHENYL)-3-METHYL-1-BUTYL] AMINOCARBONYL METHYL]BENZOATE AND USE THEREOF FOR THE PREPARATION OF REPAGLINIDE

CROSS REFERENCE TO RELATED APPLICATION

This application claims priority under 35 U.S.C. §119(a) to the application filed in the Indian Intellectual Property Office Feb. 15, 2007 and given Ser. No. 311/CHE/2007, which is hereby incorporated by reference in its entirety.

FIELD OF THE DISCLOSURE

Disclosed herein is an improved, commercially viable and industrially advantageous process for the preparation of a substantially pure Repaglinide intermediate, ethyl (S)-2-ethoxy-4-[N-[1-(2-piperidinophenyl)-3-methyl-1-butyl] aminocarbonyl methyl]benzoate. The intermediate is useful for preparing Repaglinide, or a pharmaceutically acceptable salt thereof, in high yield and purity.

BACKGROUND

U.S. Pat. No. 5,312,924 discloses a variety of phenylacetic acid benzylamide derivatives and their salts, processes for their preparation, pharmaceutical compositions comprising the derivatives, and method of use thereof. These compounds are hypoglycemic agents. Among them, Repaglinide, (S)-(+)-2-ethoxy-4-[N-[1-(2-piperidinophenyl)-3-methyl-1-butyl] amino carbonylmethyl]benzoic acid, is an oral blood glucose-lowering drug of the meglitinide class, used in the management of type 2 diabetes mellitus (also known as non-insulin dependent diabetes mellitus or NIDDM). Repaglinide lowers blood glucose levels by stimulating the release of insulin from the pancreas. This action of Repaglinide is dependent upon functioning beta (β) cells in the pancreatic islets.

Insulin release is glucose-dependent and diminishes at low glucose concentrations. Repaglinide is represented by the following structural formula:

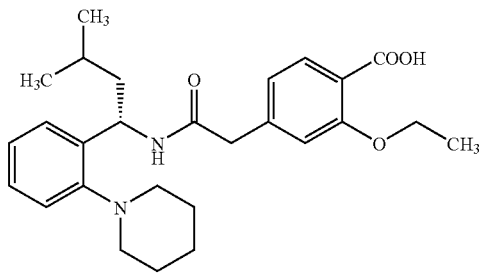

Various processes for the preparation of Repaglinide and related compounds are disclosed in U.S. Pat. No. 5,312,924, PCT Publication Nos. WO 03/027072 A1 and WO 2004/103983 A1, and U.S. Patent Application No. 2007/0123564 A1.

In the preparation of Repaglinide, ethyl (S)-2-ethoxy-4-[N-[1-(2-piperidinophenyl)-3-methyl-1-butyl]aminocarbonylmethyl]benzoate of formula I(i):

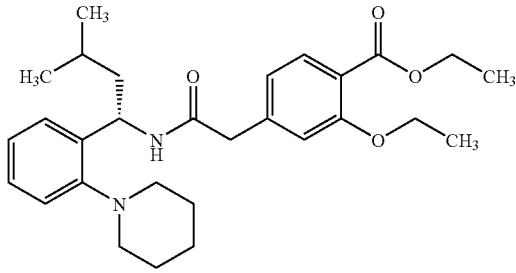

is a key intermediate. According to U.S. Pat. No. 5,312,924 (hereinafter referred to as the '924 patent), the compound of formula I(i) can be prepared by the reaction of (S)-3-methyl-1-(2-piperidinophenyl)-1-butylamine with 3-ethoxy-4-ethoxycarbonyl-phenyl acetic acid in the presence of a dehydrating agent. The dehydrating agents include ethyl chloroformate, thionyl chloride, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole or N,N'-thionyldiimidazole or triphenylphosphine/carbon tetrachloride. The reaction is performed optionally in the presence of an inorganic base such as sodium carbonate or a tertiary organic base such as triethylamine, in a solvent such as methylene chloride at a temperature of −25° C. to 250° C., preferably −10° C. to the boiling temperature of the solvent used, to produce ethyl (S)-2-ethoxy-4-[N-[1-(2-piperidinophenyl)-3-methyl-1-butyl] aminocarbonylmethyl]benzoate of formula I(i). The compound of formula I(i) is then subjected to hydrolysis in the presence of an acid or a base to produce Repaglinide.

Repaglinide obtained by the processes described in the '924 patent is generally not of satisfactory purity. Unacceptable amounts of impurities are formed during the reaction between (S)-3-methyl-1-(2-piperidinophenyl)-1-butylamine and 3-ethoxy-4-ethoxycarbonyl-phenyl acetic acid, thus resulting in a poor product yield. The process has the following disadvantages and limitations:
  i) the reagent N,N'-carbonyldiimidazole is expensive, highly moisture sensitive and yields are generally very low (50-60%);
  ii) the use of a triphenylphosphine/carbon tetrachloride combination results in an impure product, which requires multiple purification steps by re-crystallization or column chromatography. Also carbon tetrachloride is hazardous to ecosystems and human health;
  iii) the use of N,N'-dicyclohexylcarbodiimidazole (DCC) generates N, N'-dicyclohexyl urea (DCU) as by-product, which cannot be removed easily from the product. Also, N,N'-dicyclohexylcarbodiimidazole (DCC) is toxic and it is not advisable to use in a commercial scale reaction.

According to PCT Publication No. WO 03/027072 A1 (hereinafter referred to as the '072 application), the compound of formula I(i) is prepared by the reaction of (S)-3-methyl-1-(2-piperidinophenyl)-1-butylamine with 3-ethoxy-4-ethoxycarbonyl-phenyl acetic acid in the presence of pivaloyl chloride and a base.

The process used in the '072 application suffers from disadvantages such as probable racemization and high cost of reagents, the use of additional reagents such as base, low yields of the product, extra purification steps to obtain the final product, repeated crystallization and health hazards. The process is not advisable for scale up operations.

According to PCT Publication No. WO 2004/103983 A1 (hereinafter referred to as the '983 application), the compound of formula I(i) is prepared by the reaction of (S)-3-methyl-1-(2-piperidinophenyl)-1-butylamine with 3-ethoxy-4-ethoxycarbonyl-phenyl acetic acid in the presence of propane phosphonic acid anhydride.

The process used in the '983 application suffers from disadvantages such as high cost, use of additional reagents such as bases, extra purification steps to obtain the final product, multiple crystallizations, and explosive and hazardous reagents. Moreover, the Repaglinide obtained by the process described in this application does not have satisfactory purity. The use of propane phosphonic acid anhydride is not advisable for scale up operations.

Based on the aforementioned drawbacks, the prior art processes may be unsuitable for preparation of Repaglinide in commercial scale operations.

A need remains for an improved and commercially viable process of preparing a substantially pure compound of formula I(i), to resolve the problems associated with the processes described in the prior art, and that will be suitable for large-scale preparation. Desirable process properties include non-hazardous and environmentally friendly reagents, reduced cost, greater simplicity, increased purity, and increased yield of the product, thereby enabling the production of Repaglinide and its pharmaceutically acceptable acid or base addition salts in high purity and in high yield.

SUMMARY

The present inventors have surprisingly found that the Repaglinide intermediate of formula I can be prepared in high purity and with high yield by reacting (S)-3-methyl-1-(2-piperidinophenyl)-1-butylamine with a protected carboxylic acid, in the presence of a dehydrating agent selected from boric acid or boric acid derivatives, and in a suitable solvent.

In one aspect, provided herein is an efficient, convenient, commercially viable and environment friendly process for the preparation of Repaglinide intermediate, ethyl (S)-2-ethoxy-4-[N-[1-(2-piperidinophenyl)-3-methyl-1-butyl]aminocarbonylmethyl]benzoate in an 80-90% overall yield. Advantageously, the reagents used for present invention are non-hazardous and easy to handle at commercial scale and also involves less expensive reagents.

DETAILED DESCRIPTION

Provided herein is an improved process for the preparation of the Repaglinide intermediate of formula I:

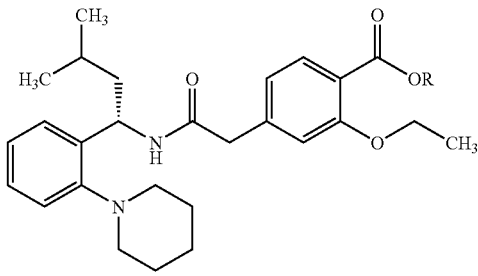

or an acid addition salt thereof, wherein the R is a protecting group, which comprises: reacting (S)-3-methyl-1-(2-piperidinophenyl)-1-butylamine of formula II:

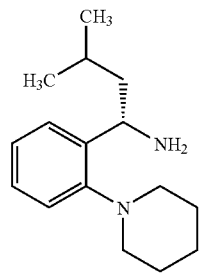

or a salt thereof with a protected carboxylic acid of formula III:

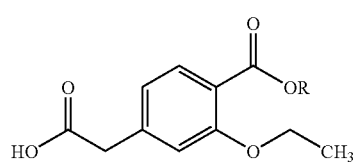

wherein R is a protecting group, in the presence of a dehydrating agent selected from boric acid or boric acid derivatives in a suitable solvent, to provide a substantially pure compound of formula I. The compound of formula I is optionally converted into its acid addition salts.

Exemplary boric acid derivatives include, but are not limited to, aryl or substituted aryl boronic acids such as phenylboronic acid, 2-chlorophenylboronic acid, 2-nitrophenyl boronic acid, 3-nitrophenylboronic acid, 4-nitrophenylboronic acid, 2-carboxyphenyl boronic acid, 2-chloro-4-carboxyphenylboronic acid, 2-chloro-5-carboxyphenylboronic acid, 3-chloro-4-carboxyphenylboronic acid, 2-chloro-4-fluorophenylboronic acid, 4-chloro-2-fluorophenylboronic acid, 2-chloro-4-methylphenylboronic acid, 2-chloro-5-methylphenylboronic acid, 2-chloro-3-methylpyridine-5-boronic acid, naphthyl boronic acid, and combinations comprising one or more of the foregoing boric acid derivatives. Specific dehydrating agents are boric acid, phenylboronic acid, and combinations comprising one or more of the foregoing dehydrating agents.

Exemplary solvents include, but are not limited to, hydrocarbons, ketones, cyclic ethers, aliphatic ethers, nitrites, alkanes, and the like, and mixtures thereof. Exemplary hydrocarbon solvents include, but are not limited to, toluene, benzene, xylene, and mixtures thereof. Exemplary ketone solvents include, but are not limited to, acetone, methyl isobutyl ketone, and the like, and mixtures thereof. Exemplary cyclic ether solvents include, but are not limited to, tetrahydrofuran, dioxane, and the like, and mixtures thereof. Exemplary nitrile solvents include, but are not limited to, acetonitrile, and the like, and mixtures thereof. Exemplary alkane solvents include, but are not limited to, n-hexane, heptane, cyclohexane, and the like, and mixtures thereof. Specific solvents are toluene, methylene chloride, tetrahydrofuran, acetonitrile, dimethylformamide, and mixtures thereof, and more specifically toluene.

The protecting group R in the compounds of formulas I and III is a carboxylic acid protecting group which is easily removed, such as methyl, ethyl, tert-butyl, benzyl, p-nitrobenzyl, p-methoxybenzyl, and the like. More specifically, the protecting group R in the compounds of formulas I and III is ethyl.

In particular, a specific compound of formula I prepared by the process described herein is ethyl (S)-2-ethoxy-4-[N-[1-(2-piperidinophenyl)-3-methyl-1-butyl]aminocarbonylmethyl]benzoate of formula I(i) or a salt thereof (formula I, wherein R is ethyl):

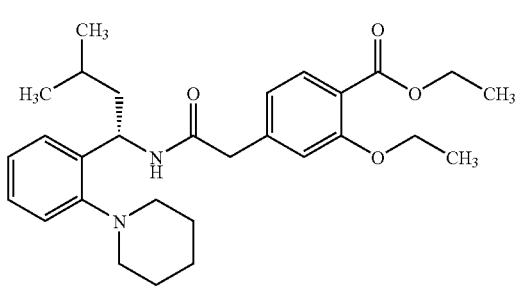

The reaction is carried out at a temperature of −25° C. to the reflux temperature of the solvent used, specifically at a temperature of 0° C. to the reflux temperature of the solvent used, more specifically at a temperature of 25° C. to the reflux temperature of the solvent used, and most specifically at the reflux temperature of the solvent used.

As used herein, "reflux temperature" means the temperature at which the solvent or solvent system refluxes or boils at atmospheric pressure.

In one embodiment, the dehydrating agent used at about 0.005 to 1.0 moles, specifically 0.1 to 0.2 moles, per 1 mole of (S)-3-methyl-1-(2-piperidinophenyl)-1-butylamine of formula II in order to ensure a proper course of the reaction.

The boric acid or boric acid derivatives used as dehydrating agents for the condensation, allows the product to be easily isolated and purified, thereby producing a product with 80-90% overall yield.

The compounds of formula I, for example, wherein the protecting group R is ethyl, and obtained by the process disclosed herein, have a purity (measured by High Performance Liquid Chromatography, hereinafter referred to as 'HPLC') greater than about 98%, specifically greater than about 99%, more specifically greater than about 99.5%, and still more specifically greater than about 99.9%.

The use of inexpensive, non-explosive, non-hazardous, readily available and easy to handle reagents allows the process disclosed herein to be suitable for preparation of Repaglinide at lab scale and in commercial scale operations.

In one embodiment, the compound of formula I obtained is isolated as solid from a suitable organic solvent by methods usually known in the art such as cooling, partial removal of the solvent from the solution, addition of precipitating solvent, or a combination thereof.

The term "substantially pure compound of formula I, wherein the protecting group R is ethyl [i.e., ethyl (S)-2-ethoxy-4-[N-[1-(2-piperidinophenyl)-3-methyl-1-butyl] aminocarbonylmethyl]benzoate of formula I(i)], or its acid addition salts" refers to the compound of formula I or its acid addition salts having purity greater than about 98%, specifically greater than about 99%, more specifically greater than about 99.5%, and still more specifically greater than about 99.9% measured by HPLC.

The compound of formula I is an amine and forms acid addition salts with organic and inorganic acids. Example of such as salts includes hydrochloride, hydrobromide, sulfate, tartarate, fumarate, mandelate and derivatives of tartaric acid.

Repaglinide and pharmaceutically acceptable acid or base addition salts of Repaglinide can be prepared in high purity by using the substantially pure compound of formula I or its acid addition salts obtained by the methods disclosed herein, by known methods, for example as described in U.S. Pat. No. 5,312,924.

HPLC Method:

The purity was measured by HPLC under the following conditions:

| | |
|---|---|
| Column | Zorbax SB-Aq (150 × 4.6 mm × 5μ) |
| Mobile phase A | 4.0 gms/Litre solution of potassium dihydrogen phosphate adjusted to pH 3.20 with dilute $H_3PO_4$ |
| Mobile phase B | Mobile phase-A, Acetonitrile (300:700 v/v). |
| Diluent | Acetonitrile. |
| Flow rate | 1.5 ml/minute. |
| Run Time | 57.0 min |
| Retention time | 35.346 |

The following examples are given for the purpose of illustrating the present disclosure and should not be considered as limitation on the scope or spirit of the disclosure.

EXAMPLE 1

Preparation of Ethyl (S)-2-ethoxy-4-[N-[1-(2-piperidinophenyl)-3-methyl-1-butyl]aminocarbonylmethyl]benzoate In a round bottom flask fitted with a dean stark condenser, (S)-3-methyl-1-(2-piperidinophenyl)-1-butylamine (10 g, 0.0406 mol) was dissolved in toluene (100 ml), followed by the addition of 3-ethoxy-4-ethoxycarbonyl phenyl acetic acid (10.26 g, 0.0407 mol) and boric acid (0.26 g, 0.0042 mol). The reaction mixture was refluxed for 16-18 hours. The resulting mass was then cooled to 25-30° C. followed by filtration. The filtrate was washed with water and 1.0% sodium bicarbonate solution followed by complete distillation of toluene and the resulting residue was stirred with hexane (50 ml) for 1 hour. The precipitated solid was filtered and washed with hexane (10 ml). The wet product was dried at 50-55° C. under vacuum for 4-6 hours to produce Ethyl (S)-2-ethoxy-4-[N-(1-(2-piperidino-phenyl)-3-methyl-1-butyl)-aminocarbonyl methyl]-benzoate (Yield=73.3%; HPLC Purity: 99.50%).

EXAMPLE 2

Preparation of Ethyl (S)-2-ethoxy-4-[N-[1-(2-piperidinophenyl)-3-methyl-1-butyl]aminocarbonylmethyl]benzoate In a round bottom flask fitted with a dean stark condenser, 3-Ethoxy-4-ethoxycarbonyl phenyl acetic acid (10.26 g, 0.0426 mol) was dissolved in toluene (100 ml) followed by slow addition of phenylboronic acid (0.494 g, 0.0040 mol) and (S)-3-methyl-1-(2-piperidinophenyl)-1-butylamine (10 g, 0.0406 mol). The reaction mixture was refluxed for 16-18 hours. The resulting mass was cooled at 25-30° C. followed by filtration. The toluene layer was washed with water and 1% sodium bicarbonate solution followed by complete distillation of toluene. Hexane (50 ml) was added to the resulting residue after complete removal of toluene in order to precipitate the solid, with stirring for 1 hour. The resulting solid was filtered and washed with hexane (10 ml). The wet material was further dried at 50-55° C. under vacuum for 4-6 hours to produce Ethyl (S)-2-ethoxy-4-[N-(1-(2-piperidino-phenyl)-3-methyl-1-butyl)-aminocarbonylmethyl]benzoate (Yield=89.6%; HPLC Purity: 99.66%).

EXAMPLE 3

Process for the Preparation of Repaglinide

Ethyl (S)-2-ethoxy-4-[N-(1-(2-piperidino-phenyl)-3-methyl-1-butyl)-amino carbonylmethyl]-benzoate (4.5 g, 0.0093 mol) was dissolved in methanol (45 ml), followed by the addition of sodium hydroxide solution (0.75 g of sodium hydroxide dissolved in 6 ml water). The reaction mixture was heated at 60-65° C. for 3-4 hours. Methanol (80-85%) was removed from the reaction mixture under vacuum. The remaining reaction mixture was diluted with water (45 ml) and pH was adjusted to 6.5-7.0 with 1N HCl. The precipitated solid was stirred for 2-3 hours followed by filtration and washing with water (45 ml). The product was further dried at 50-55° C. under vacuum for 6-8 hours to produce Repaglinide (Yield=83.2%; HPLC Purity: 99.89%).

We claim:
1. A process for preparation of Repaglinide intermediate of formula I:

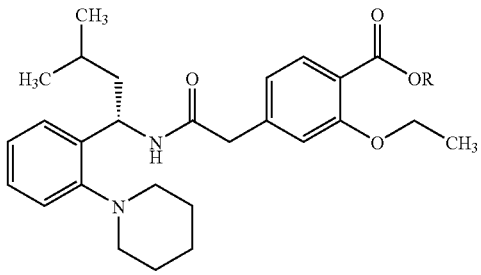

or an acid addition salt thereof, wherein the R is a protecting group, comprising:
reacting (S)-3-methyl-1-(2-piperidinophenyl)-1-butylamine of formula II:

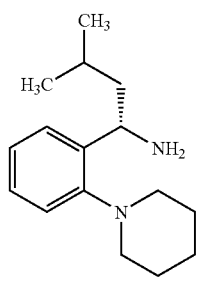

or a salt thereof with a protected carboxylic acid of formula III:

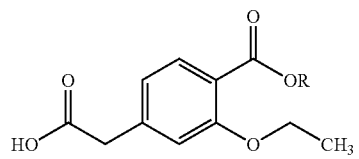

in the presence of a dehydrating agent and a suitable solvent to produce the compound of formula I;
and optionally converting the compound of formula I into its acid addition salts thereof;
wherein the dehydrating agent is an aryl or a substituted aryl boronic acid; and
wherein R is a protecting group.

2. The process of claim 1, wherein the aryl or substituted aryl boronic acid is selected from the group consisting of phenylboronic acid, 2-chlorophenylboronic acid, 2-nitrophenyl boronic acid, 3-nitrophenylboronic acid, 4-nitrophenylboronic acid, 2-carboxyphenyl boronic acid, 2-chloro-4-carboxyphenylboronic acid, 2-chloro-5-carboxyphenylboronic acid, 3-chloro-4-carboxyphenylboronic acid, 2-chloro4-fluorophenylboronic acid, 4-chloro-2-fluorophenylboronic acid, 2-chloro-4-methylphenylboronic acid, 2-chloro-5-methylphenylboronic acid, 2-chloro-3-methylpyridine-5-boronic acid, and naphthyl boronic acid.

3. The process of claim 1, wherein the solvent is selected from the group consisting of toluene, benzene, xylene, acetone, methyl isobutyl ketone, tetrahydrofuran, dioxane, acetonitrile, hexane, heptane, cyclohexane, methylene chloride, dimethylformamide, and mixtures thereof.

4. The process of claim 3, wherein the solvent is toluene, methylene chloride, tetrahydrofuran, acetonitrile, or dimethylformamide.

5. The process of claim 4, wherein the solvent is toluene.

6. The process of claim 1, wherein the protecting group R is methyl, ethyl, tert-butyl, benzyl, p-nitrobenzyl, or p-methoxybenzyl.

7. The process of claim 6, wherein the protecting group R is ethyl.

8. The process of claim 1, wherein the reaction is carried out at a temperature of −25° C. to a reflux temperature of the solvent.

9. The process of claim 1, wherein the dehydrating agent is used in a molar ratio of 0.005 to 1.0 moles relative to 1 mole of the (S)-3-methyl-1-(2-piperidinophenyl)-1-butylamine of formula II.

10. The process of claim 9, wherein the dehydrating agent is used in a molar ratio of 0.1 to 0.2 moles relative to 1 mole of (S)-3-methyl-1-(2-piperidinophenyl)-1-butylamine of formula II.

11. The process of claim 1, wherein the compound of formula I obtained has a purity of greater than 99% as measured by HPLC.

12. The process of claim 11, wherein the compound of formula I obtained has a purity of greater than 99.9% as measured by HPLC.

* * * * *